US010260856B2

(12) United States Patent
Featherstone

(10) Patent No.: US 10,260,856 B2
(45) Date of Patent: Apr. 16, 2019

(54) METHOD OF INSPECTING AN OBJECT WITH A CAMERA PROBE

(71) Applicant: RENISHAW PLC, Wotton-under-Edge, Gloucestershire (GB)

(72) Inventor: Timothy Charles Featherstone, Edinburgh (GB)

(73) Assignee: RENISHAW PLC, Wotton-Under-Edge (GB)

(*) Notice: Subject to any disclaimer, the term of this patent is extended or adjusted under 35 U.S.C. 154(b) by 70 days.

(21) Appl. No.: 15/025,418

(22) PCT Filed: Oct. 2, 2014

(86) PCT No.: PCT/EP2014/071176
§ 371 (c)(1),
(2) Date: Mar. 28, 2016

(87) PCT Pub. No.: WO2015/049341
PCT Pub. Date: Apr. 9, 2015

(65) Prior Publication Data
US 2016/0238373 A1  Aug. 18, 2016

(30) Foreign Application Priority Data
Oct. 3, 2013   (EP) .................................. 13275242

(51) Int. Cl.
H04N 7/18   (2006.01)
G01B 11/00  (2006.01)
(Continued)

(52) U.S. Cl.
CPC ............ *G01B 11/005* (2013.01); *G01B 11/24* (2013.01); *G01B 21/047* (2013.01);
(Continued)

(58) Field of Classification Search
CPC ....................................................... H04N 19/00
(Continued)

(56) References Cited

U.S. PATENT DOCUMENTS 5,125,035 A    6/1992  McCarthy et al.
5,251,156 A *  10/1993 Heier .................. G01B 11/005
                                                    33/503
(Continued)

FOREIGN PATENT DOCUMENTS

CN    102803893 A   11/2012
EP      2385364 A1  11/2011
(Continued)

OTHER PUBLICATIONS

Xing-Fei He et al., "Time Delay Integration Speeds Up Imaging", Photonics Spectra, 2012.
(Continued)

Primary Examiner — Anand S Rao
(74) Attorney, Agent, or Firm — Oliff PLC

(57) ABSTRACT

A method of inspecting an object with a camera probe for capturing an image of an object, the camera probe being movable along a path by a measurement apparatus, at least a part of the camera probe being rotatable about at least one axis. The method includes: a) the measurement apparatus moving the camera probe relative to the object along an inspection path and b) for at least one period as the camera probe moves along the inspection path: turning at least a part of the camera probe about the at least one axis thereby slowing the passage of a feature of interest on the object across the camera probe's field of view; and capturing at least one image of the feature of interest during at least a portion of the turning.

19 Claims, 5 Drawing Sheets

(51) Int. Cl.
*G01B 21/04* (2006.01)
*G01N 21/88* (2006.01)
*G01B 11/24* (2006.01)

(52) U.S. Cl.
CPC ......... *G01N 21/8806* (2013.01); *H04N 7/183* (2013.01); *G05B 2219/37063* (2013.01); *G05B 2219/37199* (2013.01); *G05B 2219/37572* (2013.01)

(58) Field of Classification Search
USPC .................................. 348/80–110, 125–145
See application file for complete search history.

(56) References Cited

U.S. PATENT DOCUMENTS

| | | | |
|---|---|---|---|
| 5,442,438 | A | 8/1995 | Batchelder et al. |
| 5,689,333 | A | 11/1997 | Batchelder et al. |
| 5,982,491 | A | 11/1999 | Breyer et al. |
| 7,489,811 | B2 | 2/2009 | Brummel et al. |
| 8,305,571 | B2 | 11/2012 | Smith |
| 9,618,329 | B2 | 4/2017 | Weston et al. |
| 2003/0048933 | A1 | 3/2003 | Brown et al. |
| 2003/0213868 | A1 | 11/2003 | Brunner et al. |
| 2005/0151963 | A1 | 7/2005 | Pulla et al. |
| 2007/0073439 | A1 | 3/2007 | Habibi et al. |
| 2007/0276629 | A1 | 11/2007 | Koonankeil |

FOREIGN PATENT DOCUMENTS

| | | |
|---|---|---|
| JP | 2011-526375 A | 10/2011 |
| WO | 02/070211 A1 | 9/2002 |
| WO | 2008/090350 A1 | 7/2008 |
| WO | 2009/024783 A1 | 2/2009 |
| WO | 2009/093050 A1 | 7/2009 |
| WO | 2010/139950 A1 | 12/2010 |
| WO | 2014/122438 A1 | 8/2014 |

OTHER PUBLICATIONS

Ostman, "TDI CCDs are still the sensors of choice for demanding applications", Laser Focus World, pp. 1-6, 2010.
Dec. 11, 2014 International Search Report issued in International Patent Application No. PCT/EP2014/071176.
Dec. 11, 2014 Written Opinion issued in International Patent Application No. PCT/EP2014/071176.
Mar. 17, 2014 Search Report issued in European Patent Application No. 13275242.9.
Jul. 31, 2018 Office Action issued in Japanese Patent Application No. 2016-520031.
Feb. 23, 2018 Office Action issued in Chinese Patent Application No. 201480065697.9.
Dec. 3, 2018 Office Action issued in Chinese Patent Application No. 201480065697.9.

* cited by examiner

METHOD OF INSPECTING AN OBJECT WITH A CAMERA PROBE

The present invention relates to a method of inspecting an object, in particular with a camera probe.

Camera probes are known for capturing images of an object to be inspected. The camera probe is moved about the object, e.g. by a movement apparatus, and collects images of the object. At some point (e.g. could be immediately after they are captured or at some time after collection) the images are processed to determine information about the object. This could be by a processor on the camera probe, or external to the camera probe.

In some situations it is desirable to use the camera probe to inspect select features on the object as the camera probe moves about the object. For example, it might be desirable to inspect one or more holes, or bores, in an object, e.g. to determine their size and/or form. However, it has been found that image blurring can be a significant adverse factor when trying to image select features. Stopping the motion of the camera probe along an inspection path can substantially eliminate blurring, but dramatically increases inspection time due to the start-stop nature of the motion.

US2003/0213868 discloses a camera system for tracking a target from an aircraft such that the pilot or a passenger can observe a point of interest on the aircraft or on the ground. WO2010/139950 discloses a video probe mounted on an articulated head of a coordinate measuring machine. US2007/0073439 discloses a machine vision system for tracking a workpiece that is transported on a conveyer track in an assembly line. U.S. Pat. No. 5,982,491 discloses an optical probe for inspecting the edges of a workpiece. EP2385364 discloses a method of visually inspecting features on a workpiece which involves reorienting the part to align the feature with respect to a camera before an image is obtained.

The present invention provides an improved technique for obtaining images of select features on an object as a camera probe is moved about an object. For example, the technique involves the camera probe and object being relatively movable by a measurement apparatus, at least a part of the camera probe being rotatable about at least one axis, and: a) the measurement apparatus relatively moving the camera probe and object; b) for at least one period during said relative movement: turning at least a part of the camera probe about the at least one axis and capturing at least one image whilst turning the camera probe about the at least one axis. In other words, the technique involves the camera probe being movable along a path by a measurement apparatus, at least a part of the camera probe being rotatable about at least one axis, and: a) the measurement apparatus moving the camera probe relative to the object along an inspection path; b) for at least one period as the camera probe moves along the inspection path: turning at least a part of the camera probe about the at least one axis and capturing at least one image whilst turning the camera probe about the at least one axis.

For example, the invention provides an improved technique for obtaining images of select features of an object as a camera probe and object are moved relative to each other, in which the camera probe is configured to track the feature of interest as the feature and camera probe pass. In other words, the invention provides an improved technique for obtaining images of select features of an object as a camera probe and object are moved relative to each other, in which the camera probe is turned so as to keep the camera probe targeted on the feature of interest they pass. In other words, the invention provides an improved technique for obtaining images of select features of an object as a camera probe is moved about an object, in which the camera probe is configured to track the feature of interest as it passes the feature of interest. In other words, the invention provides an improved technique for obtaining images of select features of an object as a camera probe is moved about an object, in which the camera probe is turned so as to keep the camera probe targeted on the feature of interest as it passes the feature of interest.

According to a first aspect of the invention there is provided a method of inspecting an object with a camera probe for capturing an image of an object, the camera probe and object being relatively movable by a measurement apparatus, at least a part of the camera probe being rotatable about at least one axis, the method comprising: a) the measurement apparatus relatively moving the camera probe and the object; b) for at least one period during said relative movement: turning at least a part of the camera probe about the at least one axis thereby slowing the passage of a feature of interest on the object across the camera probe's field of view; and capturing at least one image of the feature of interest during at least a portion of said turning. In other words, there is provided a method of inspecting an object with a camera probe for capturing an image of an object, the camera probe being movable along a path by a measurement apparatus, at least a part of the camera probe being rotatable about at least one axis, the method comprising: a) the measurement apparatus moving the camera probe relative to the object along an inspection path; b) for at least one period as the camera probe moves along the inspection path: turning at least a part of the camera probe about the at least one axis, thereby slowing the passage of the feature of interest across the camera probe's field of view; and capturing at least one image of the feature of interest (as the at least a part of the camera probe is turned about the at least one axis).

Accordingly, the invention utilises rotational motion of at least a part of the camera probe which can help to enable images of select features to be obtained with significantly reduced blurring. Turning at least a part of the camera probe can help to counter the relative motion along the inspection path and can help keep the camera probe targeted on the feature of interest (e.g. as it approaches and/or passes the feature of interest). In other words, the camera probe can track the feature of interest during such turning motion.

The present invention can help overcome problem of image sheer when the image is obtained using a rolling shutter technique. Furthermore, as mentioned above, blurring caused by relative motion of the camera and object can be a significant adverse factor and stopping the relative motion is an effective way to avoid blurring. However, the present invention can help to avoid the need to reduce the velocity (e.g. of the camera probe) along the inspection path without reducing the quality of the images being obtained. Furthermore, it enables relatively long exposure times to be maintained if desired, (e.g. it allows a relatively slow camera to be used if desired). For example, an exposure duration of at least 5 ms (milliseconds), for example 10 ms, and even for instance 20 ms or 30 ms or longer are possible whilst still maintaining sufficient image quality, and even whilst the camera and object move relative to each other at a relatively high speed (e.g. at a relative velocity of at least 25 mm/s (millimeters per second), for instance at least 35 mm/s, and even for example at least 50 mm/s during image acquisition). It can be advantageous to maintain an exposure duration of at least 5 ms, for example 10 ms or more, because the longer the exposure duration the more light that is collected, which can improve image quality. However, the longer the exposure duration, the more likely that significant blurring will occur which can itself adversely affect the image quality. The invention reduces this issue by turning at least a part of the camera probe so as to slow the passage of the feature of interest on the object across the camera probe's field of view (and hence slow the passage of the image of the feature of interest across the camera probe's image sensor). This can be useful in a number of situations. As one example, sometimes a large depth of field is desired, which can be achieved using a small aperture, hence restricting the amount of light received by the camera probe's sensor. In such cases a longer exposure duration can be desired in order to maintain sufficient light collection.

Accordingly, the invention enables continuous relative motion of the camera probe and object, i.e. it doesn't require interruption of motion (e.g. substantially stopping) to acquire an image. This can be particularly advantageous because it can enable continuous motion during image acquisition and also when moving between features. Further still, the invention enables a reasonable (and for example, constant) speed to be maintained (during and between acquisition of images of features of interest) since the invention enables good images to be obtained at a reasonable speed (e.g. at a relative velocity of at least 25 mm/s). The present application makes reference to the camera probe "tracking" or "targeting" the feature of interest (such terms being used interchangeably). As will be understood, such tracking/targeting can be "active" or "passive". For example, in the case of "active" tracking/targeting, the rotational motion of the camera probe can be continuously adjusted based on live/real-time information received (e.g. from the camera probe itself) about the actual relative positional relationship between the feature of interest and camera probe, and the course of motion of the camera probe can be tweaked accordingly. For example, an image processor could analyse images obtained by the camera probe so as to identify the presence/location of the feature of interest within the image, based on which real-time feedback information can be obtained and used to automatically servo the motion of the camera probe such that the camera probe is locked on the feature of interest. In the case of "passive" tracking, such real-time feedback information is not used and hence the feature of interest is tracked/targeted by virtue of predetermined/assumed knowledge of the approximate position of the feature of interest and the camera probe being controlled according to a predetermined course of motion. Accordingly, in the "passive" tracking embodiments, a technique more akin to dead-reckoning can be used to track the feature of interest.

The camera probe can comprise at least one sensor. The camera probe can comprise at least one lens for forming an image on the sensor. At least one optical part of the camera probe can be rotatable about the at least one axis. For example, at least one of said at least one sensor and at least one lens can be rotatable about the at least one axis so that the camera probe tracks a feature of interest on the object. Optionally, a mirror within the camera probe can rotate the image picked up by the camera probe and projected onto the sensor. Optionally, the camera probe itself is rotatable about the at least one axis. At least a part of the measurement apparatus can be rotatable about at least one axis. Accordingly, the camera probe can be rotated by the measurement apparatus about the at least one axis.

Accordingly, the camera probe can be mounted on a rotatable part of the measurement apparatus. The camera probe can be mounted on an articulated head of the measurement apparatus. The articulated head can comprise at least one rotational axis, optionally at least two rotational axes for example at least three rotational axes. The first, second and optionally third rotational axes can be arranged orthogonal relative to each other. Optionally, the articulated head is mounted on a frame configured to provide movement of the articulated head in at least one linear dimension, optionally at least two linear dimensions, for example at least three linear dimensions. The first, second and optionally third linear dimensions can be arranged orthogonal relative to each other.

As will be understood, the measurement apparatus can provide a measure of the position and/or orientation of the camera probe, in particular at least at the point images are obtained.

The measurement apparatus can comprise an object support and a camera probe support. The measurement apparatus can be configured to effect relative movement between the object support and camera probe support. For example, the measurement apparatus can comprise a platform (in other words a table or bed) for the object and a mount for the camera probe. The camera probe support and/or the object support can be part of a moveable part of the measurement apparatus. For example, the camera probe support can be part of a moveable quill, bridge or arm of a measurement apparatus and/or the object support can be part of a moveable platform and/or rotary table.

As will be understood, another term for a measurement apparatus is a measurement machine.

The measurement apparatus can comprise a coordinate position machine, for example machine tool or a coordinate measuring machine (CMM). Such apparatus include, gantry, bridge and arm type measurement apparatus, and includes robot arms. Preferably, the measurement apparatus can move the camera probe and object relative to each other (e.g. along a measurement/inspection path) automatically under the control of a controller. The controller could be operated according to a program which comprises (e.g. camera probe) course of motion instructions.

The method can comprise capturing at least one image of the feature of interest at a predetermined relative position and/or angular orientation between the camera and feature of interest. The method can comprise turning at least a part of the camera probe about the at least one axis (e.g. so that the camera probe tracks the predetermined feature of interest on the object) before and/or after the predetermined relative position.

For example, when the feature of interest is a bore, the predetermined relative position and/or angular orientation can be when the camera probe's optical axis is parallel, and preferably coaxial, with the bore's central axis. Accordingly, when using the present invention, the camera probe's optical axis can pivot about a point on the bore's central axis.

The predetermined relative position and/or angular orientation between the camera and feature of interest can be defined with respect to a predetermined plane (e.g. a plane of interest on the object) which at least partly contains the feature of interest. The predetermined relative position and/or angular orientation between the camera and feature of interest can be when the camera probe's optical axis is perpendicular to the predetermined plane of interest.

As will be understood, the capture duration (also referred to herein as exposure time) of the at least one image can be less, and for example significantly less, than the time during which the at least a part of the camera probe is turned. Optionally, a plurality of images (e.g. at least two images) of the feature of interest are captured whilst the at least a part of the camera probe is turned. In other words, the method can comprise capturing a plurality images of the predetermined feature of interest whilst the at least a part of the camera probe is turned (e.g. so as to track the predetermined feature of interest).

During such turning, the feature of interest can be kept within the camera probe's field of view. Optionally, during such turning the feature of interest is kept substantially laterally stationary within the camera probe's field of view. Optionally, during such turning the feature of interest is kept in the centre of the camera probe's field of view.

Optionally, the camera probe is moved relative to the feature of interest so as to keep the feature of interest within the camera probe's depth of field during such turning. In particular for camera probes having a narrow depth of field, this can require moving the camera probe in an arcuate motion during such rotation, about the feature of interest.

The camera probe's optical axis can lead the camera probe (e.g. along an inspection path) as the camera probe approaches the feature of interest and/or can trail the camera probe (e.g. along the inspection path) as the camera probe passes the feature of interest (e.g. so as to track the predetermined feature of interest). Accordingly, the angle between the camera probe's optical axis and the path of relative motion (e.g. the inspection path) can vary such that the camera probe is aimed at the feature of interest before, during and after the camera probe and feature of interest pass each other. In other words, the camera probe can be configured so as to look toward the feature of interest as they approach each other and/or look pass each other. As will be understood and as described elsewhere in this application, the camera probe can be turned continuously so as to track the feature of interest before and/or after they pass each other.

Such turning can comprise controlling the camera probe such that the camera probe pivots about a point in the camera probe's depth of field, and optionally about a point on the camera probe's object plane.

The method can comprise, for each of a plurality of features of interest on the object (e.g. along an inspection path), the measurement apparatus turning at least a part of the camera probe about the at least one axis (e.g. so as to track the feature of interest), thereby slowing the passage of the feature of interest past the camera probe's field of view, and capturing at least one image of the feature of interest.

The feature(s) of interest can be a predetermined feature of interest. The feature of interest could for example comprise any area, region, line, edge or other feature on the object. The feature could be a distinct feature, or could comprise a particular region or patch on a generally uniform, smooth or unremarkable surface. The feature of interest can comprise a bore. The feature of interest can comprise a particular region of a bore, for example, the mouth of a bore.

The method can comprise analysing the at least one image to determine measurement data concerning the feature of interest.

The method can comprise reporting and/or recording the relative position of the camera probe and the object. The method can comprise the measurement apparatus reporting and/or recording the position and/or orientation of the camera probe. The method can comprise the measurement apparatus reporting and/or recording the position and/or orientation of the camera probe during the image capture. The method can comprise the measurement apparatus reporting and/or recording the position and/or orientation of the camera probe at the predetermined acquisition point.

In any case, the method can comprise using the at least one image, and position data obtained from the measurement apparatus regarding the relative position of the camera probe and the object in order to obtain measurement data concerning the feature of interest.

In embodiments in which a plurality of images is obtained of the feature of interest, the method can further comprise using at least two images in a stereo-photogrammetry process (e.g. in order to obtain three-dimensional point measurement data).

Optionally, the object is stationary. Accordingly, the camera probe can be moved by the measurement apparatus relative to the stationary object, e.g. along an inspection path. Optionally, the object moves, at least during said capturing of the at least one image. In this case, the camera probe need not necessarily move (other than said required rotation of at least part of the camera probe). Accordingly, the object, in particular the feature(s) of interested on the object, can move along an inspection path. Optionally, such movement comprises rotational movement. For example, the object could be rotated, at least during said capturing of the at least one image. In some embodiments, both the camera probe and object can move, at least during said capturing of the at least one image. Accordingly, in this case an inspection path pertains to the motion of both the camera probe and object (in particular the motion of the feature(s) of interest on the object).

According to a second aspect of the invention there is provided, an apparatus for inspecting an object comprising a camera probe mounted on a measurement apparatus, at least a part of the camera probe being rotatable about at least one axis, the apparatus comprising a controller which is configured to control the measurement apparatus so as to move the camera probe relative to the object along an inspection path, and, for at least one period as the camera probe moves along the inspection path turn said at least a part of the camera probe about the at least one axis so that the camera probe tracks a predetermined feature of interest on the object thereby slowing the passage of the feature of interest across the camera probe's field of view, and configured to control the camera probe so as to capture at least one image of the feature of interest.

According to a third aspect of the invention there is provided a computer program code comprising instructions which when executed by a controller of a measurement positioning apparatus causes the measurement apparatus to operate in accordance with the above described methods.

According to a fourth aspect of the invention there is provided a computer storage medium comprising computer program code which when executed by a controller of a measurement positioning apparatus causes the measurement apparatus to operate in accordance with the above described methods.

Embodiments of the invention will now be described, by way of example only, with reference to the following drawings in which.

Figure 1:
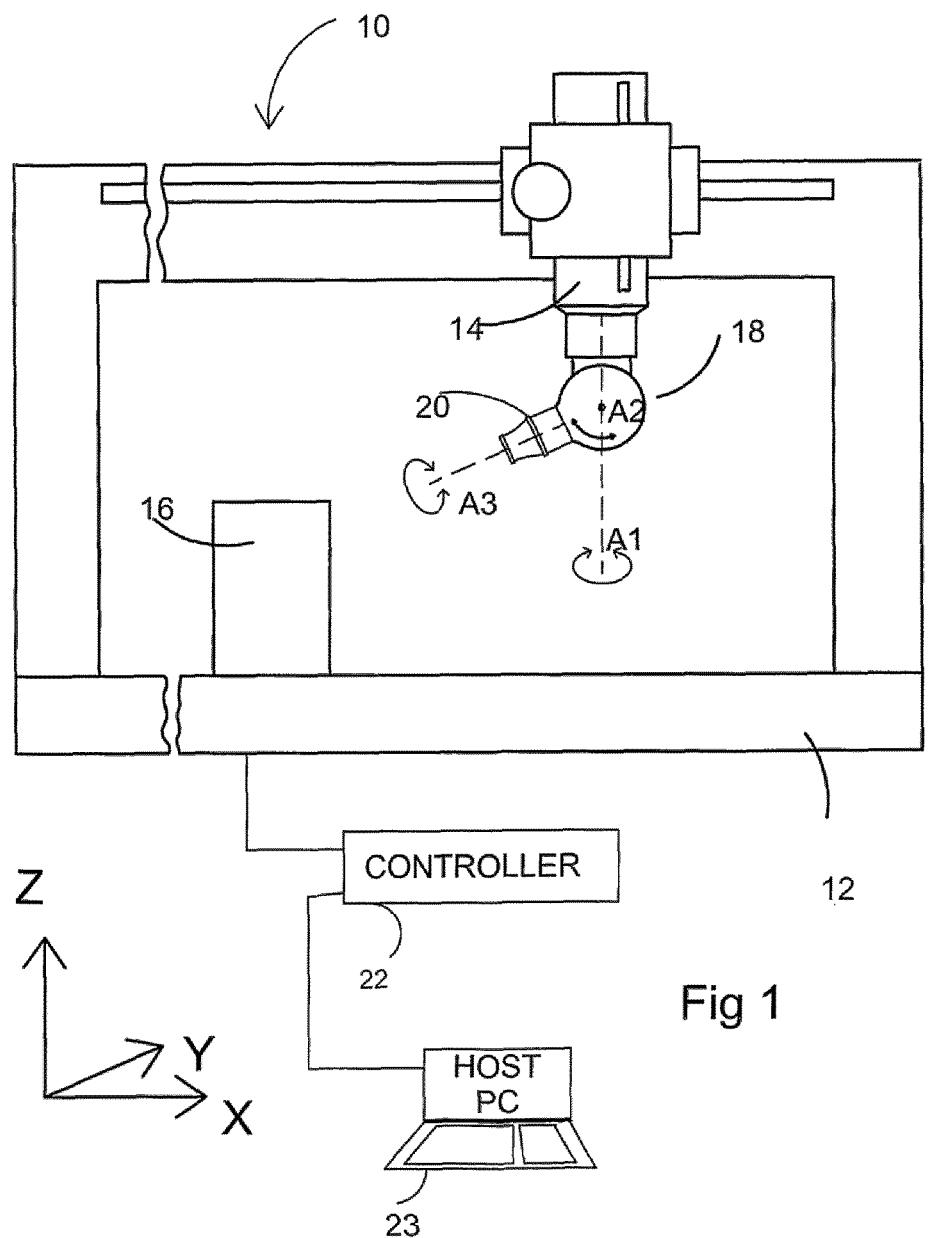
FIG. 1 illustrates of a camera probe mounted on an articulated head of a coordinate measuring machine (CMM) for measuring an object.

FIG. 1 illustrates an object inspection apparatus according to the invention, comprising a coordinate measuring machine (CMM) 10, a camera probe 20, a controller 22 and a host computer 23. The CMM 10 comprises a table 12 onto which an object 16 can be mounted and a quill 14 which is movable relative to the table 12 in three orthogonal linear dimensions X, Y and Z. An articulated probe head 18 is mounted on the quill 14 and provides rotation about at least two orthogonal axes A1, A2. The camera probe 20 is mounted onto the articulated probe head 18 and is configured to obtain images of the object 16 located on the table 12. The camera probe 20 can thus be moved in X, Y and Z by the CMM 10 and can be rotated about the A1 and A2 axes by the articulated probe head 18. Additional motion may be provided by the CMM or articulated probe head, for example the articulated probe head may provide rotation about the longitudinal axis of the video probe A3.

The desired trajectory/course of motion of the camera probe 20 relative to the object 16 is calculated by the host computer 23 and fed to the controller 22. Motors (not shown) are provided in the CMM 10 and articulated probe head 18 to drive the camera probe 20 to the desired position/orientation under the control of the controller 22 which sends drive signals to the CMM 10 and articulated probe head 18. The positions and orientations of the various axes of the CMM 10 and the articulated probe head 18 are determined by transducers, e.g. position encoders, (not shown) and the positions are fed back to the controller 22. As explained below, the positions and orientation information can be used during the obtaining of metrological information about a feature of interest.

Figure 2:
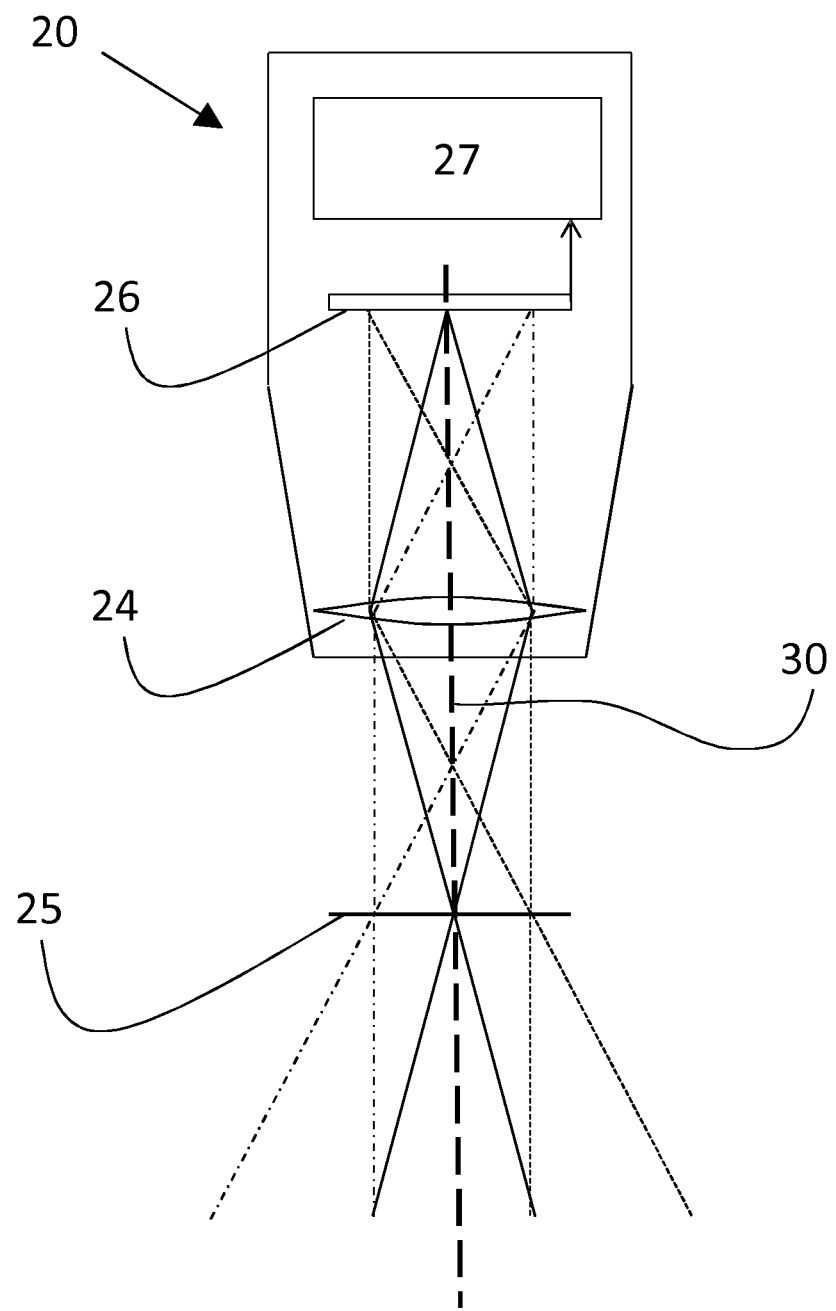
FIG. 2 illustrate a camera probe for use with the present invention.

An example of a camera probe 20 suitable for use with the invention is shown in FIG. 2. FIG. 2 is a simplified diagram showing the internal layout of a camera probe. As illustrated by the schematic ray diagram, lens 24 is configured to form an image of whatever is located at its (and hence the camera probe's) object plane 25 onto a sensor 26. As illustrated, in this embodiment, the object plane 25 is perpendicular to the lens' (and hence the camera probe's) optical axis 30. In this embodiment, the sensor 26 is a 2-dimensional pixelated sensor, such as a charge coupled device ("CCD"). As will be understood, sensors other than CCDs can be used, for example a complementary metal-oxide-semiconductor ("CMOS") array.

The camera probe 20 could comprise one or more light sources for illuminating the object. For instance, a one or multi-dimensional array of light emitting diodes ("LEDs") could be provided so as to provide broad illumination of the object. Furthermore, a light source could be provided so as to provide spot illumination of the object. Examples of camera probes including such illumination techniques are disclosed in WO2010/139950. Optionally, the object could be illuminated using light sources separate from the probe, for example a backlight (e.g. such as described in WO2014/122438)

Image data from the sensor 26 is passed to a processor device 27. The processor device could perform some processing on the image (e.g. compression of the image and/or image analysis, etc) and send the processed data to the controller 22 and/or host PC 23 (e.g. via a wired or wireless connection) or simply send raw image data back to the controller 22 and/or host PC 23. Optionally, the processor device could itself analyse the image data from the sensor to obtain measurement information.

Figure 3A:
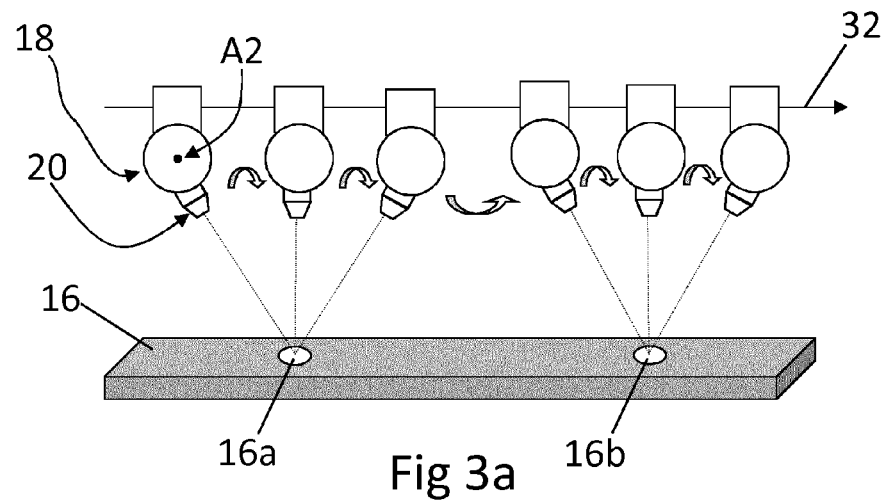
FIGS. 3a, 3b and 3c illustrate a camera probe turning so as to track multiple features at different periods in time according to the present invention.

The method of the invention will now be described in connection with FIGS. 3a to 3c. Referring to FIG. 3a, object 16 comprises first 16a and second 16b features of interest, which in this case are holes in the object 16. The camera probe 20 is configured to move relative to the object along an inspection path 32, in this case a straight line parallel to the outer surface of the object 16.

It is desired to obtain at least one image of each of the features of interest (i.e. in this case the first 16a and second 16b holes). In particular, it is desired to obtain at least one image of each feature of interest on the object 16 at a predetermined positional relationship between the camera 20 and the feature of interest (the hole) on the object 16. This predetermined positional relationship could be called the predetermined acquisition point. In the present example, the predetermined acquisition point is when the camera's optical axis 30 is coincident with the axis of the hole.

In order to achieve this, the camera probe 20 is moved in a continuous motion along the inspection path 32 by moving the quill 14 (onto which the articulated head 18 and camera probe 20 are mounted) along at least one of the CMM's three orthogonal axes X, Y, Z. In this case, this is achieved by moving the quill 14 along the X axis in a continuous motion (i.e. without stopping), but could additionally or alternatively be moved in the Y and/or Z axes too. Optionally, not only is the motion continuous but the quill is moved at a constant velocity (for example, at at least 25 mm/s but can be for example at at least 50 mm/s or more). At the same time as such lateral motion along the X, Y and/or Z axes, the articulated head is controlled so as to rotate the camera probe 20 about its A2 axis such that for a period before and a period after the predetermined acquisition point, the feature of interest (e.g. the hole) is kept in the centre of the camera probe's 20 field of view. In this embodiment, such rotation of the camera probe 20 is continuous, i.e. not start-and-stop. However, in this described embodiment the rotational speed or angular velocity of the camera probe 20 is not constant, in that the rotational rate increases as it approaches the predetermined acquisition point and decreases as it passes the predetermined acquisition point.

Accordingly, for a period as the camera probe 20 moves along the inspection path, the camera probe 20 is rotated by the articulated head so as to keep it targeted on the feature of interest (the hole 16a) on the object 16.

In this embodiment such targeting/tracking of the feature of interest is done "passively". That is, the approximate position of the feature of interest (e.g. the hole 16) is known or assumed by the controller 22 and/or computer 23 and so the camera probe's 16 motion can be controlled so as to track/target the feature of interest as it passes the feature of interest based on the known or assumed position. For instance, a user could input the location of the known/assumed position to the host computer 23 and the motion of the camera probe can be controlled such that it turns so as to track the feature at that location. Alternatively, at a set up/registration/part alignment stage, the location of the object 16 within the CMM's 10 measurement volume can be determined and hence the controller 22 and/or computer 23 can deduce the approximate position of one or more features of interest (e.g. hole 16a) based on a model (e.g. a CAD model) of the part to be inspect. In these cases, a dead-reckoning type approach is used to implement such tracking/targeting of the feature of interest. As will be understood, in contrast to such passive tracking/targeting, the tracking/ targeting could be done "actively" in which real-time feedback is used in the determination of how to move the camera probe so as to keep it locked onto the feature of interest. For example, a predetermined course of motion of the camera probe could be determined based on assumed/known position information regarding the object and/or feature of interest, but real-time feedback data (e.g. obtained by image processing images obtained by the camera probe) could be used to tweak the motion so as to ensure that the camera probe is locked onto the feature of interest as it passes the feature of interest.

In this embodiment, the camera probe turns so as to track/target the feature of interest for a period both before and after the predetermined acquisition point. As will be understood, such turning so as to track/target before and after need not be necessary and the advantage of the invention can be obtained by only turning before or after the predetermined acquisition point. For example, the turning so as to track/target could begin at the predetermined acquisition point/at the beginning of when an image is acquired, or alternatively end at the predetermined acquisition point/at the end of when an image is acquired.

However, it has been found that such turning motion can be less stable as it starts and stops and hence a more stable image can be obtained by avoiding capturing an image during the beginning and end periods of the turning motion. In the embodiment described, the capture duration/exposure time is less than the duration over which the camera probe is turned. As will be understood, the exact proportions can vary based on many different factors including how quickly the turning motion becomes stable and how long an exposure is needed in order to obtain sufficient light (which can depend on factors such as lighting). In any case, by way of example only, the image could be captured for less than half the time the feature is actually being tracked, and for example as little as less than a $10^{th}$ of the time the feature is actually being tracked.

If desired, more than one image can be obtained whilst the camera is being turned. Multiple images can be obtained and used for various different reasons, including for stereo imaging/stereo photogrammetry purposes. However, as will be understood, this need not necessarily be the case and for example only one image could be obtained, and in particular this one image could be obtained during most if not the whole time whilst the camera probe is being turned.

Figure 3B:
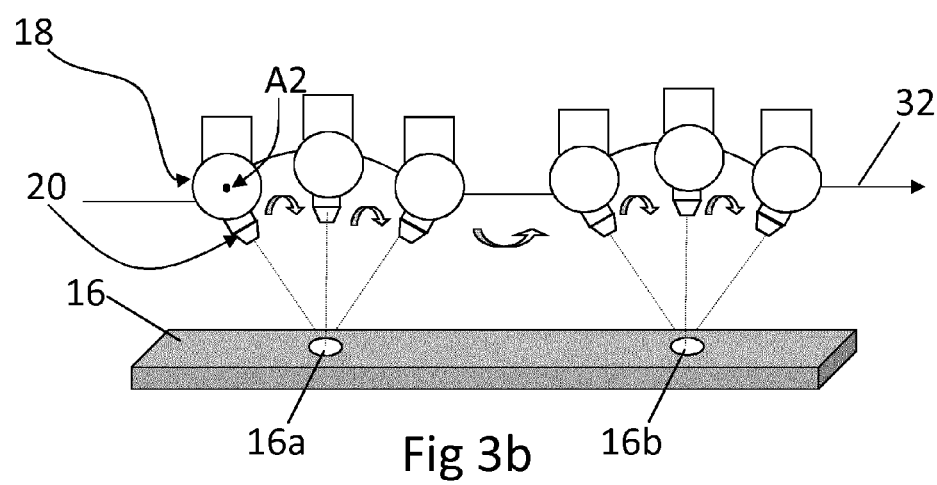
Figure 3C:
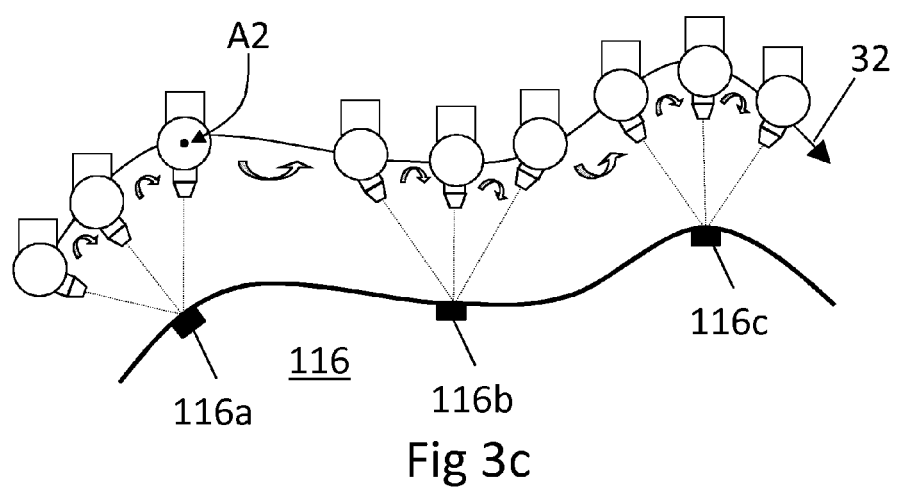

FIGS. 3b and 3c show slightly different embodiments. In FIG. 3b the inspection path is arranged such that during the period which the feature of interest is tracked by the camera probe, the probe is moved along the X, Y and/or Z axes so as to maintain the camera probe's 20 object plane 26 at the feature of interest. This can be especially advantageous for embodiments in which the camera probe's 20 depth of field is particularly shallow. As shown in FIG. 3b, this can require moving the quill 14 in an arcuate path during the period which the feature of interest is tracked.

FIG. 3c shows that the invention being used to track a series of features of interest 116a, 116b, 116c on a non-planar face of an object 116. Again, as shown, the camera probe 20 is turned so as to track a feature of interest whilst the quill 14 moves the articulated head 18 and hence camera probe 20 along the inspection path 32 which in this case follows the general contour of the object 116 (as will be understood the inspection path need not necessarily follow the general contour of the object).

As will be understood, if the camera probe 20 was not configured so as to track the feature of interest, the feature of interest would pass across the camera probe's image sensor 26 at the same velocity that the camera probe is moved relative to the object 16. Such above described tracking of the feature of interest according to the invention slows the passage of the feature of interest across the camera probe's image sensor 26. In fact, the motion of the camera probe 20 can be controlled such that there is substantially no relative lateral velocity between the camera probe's field of view and the feature of interest, at least at the predetermined acquisition point.

Figure 4:
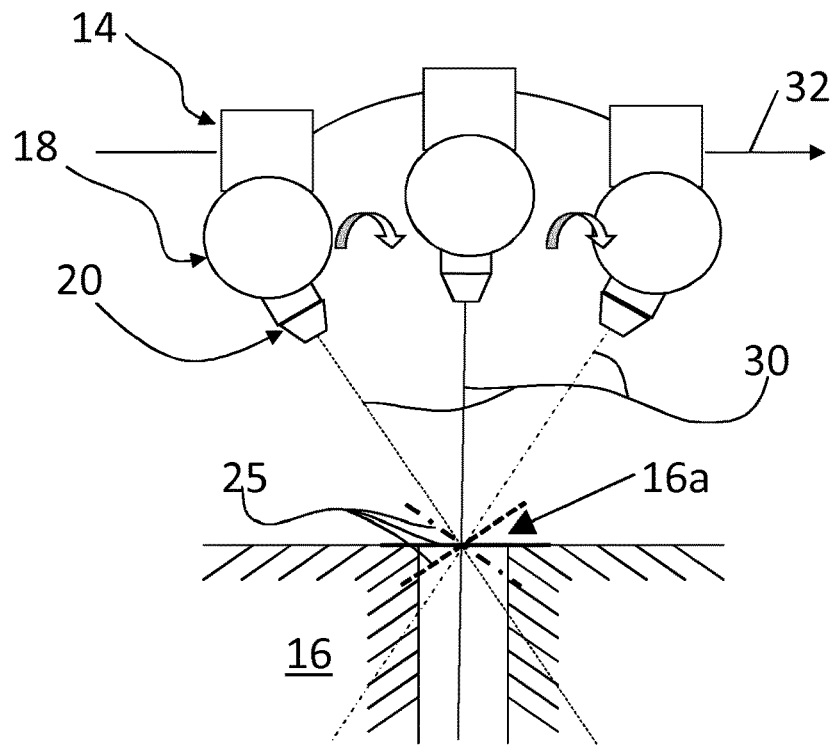
FIG. 4 illustrates a camera probe turning so as to track a feature on an object being inspected according to the present invention.

Indeed, as illustrated in more detail in FIG. 4 the feature of interest to be imaged is the mouth of the hole 16a. The arcuate motion of the quill 14 along the inspection path 32, combined with the rotational motion of the camera probe 20 about the A2 axis of the articulated head 18 means that the camera probe's 20 object plane 25 pivots about the centre of the mouth of the hole 16a. Accordingly, in this case there is no lateral velocity between the camera's 20 object plane 25 and the feature of interest (i.e. the mouth of the hole 16a), and hence no lateral velocity between the camera's field of view and the feature of interest (in other words, the centre of the feature of interest does not laterally move within the camera's field of view).

Such motion of the quill 14 and rotation of the articulated head 18 is controlled by the controller 22 controlling the CMM 10. The controller 22 can be executing a measurement program created by the host PC 23, for example.

The image(s) of the feature of interest obtained by the camera probe 20 can be processed in order to determine metrology information about the feature of interest. For instance, in the described embodiment the image(s) can be analysed to determine the diameter of the hole 16a. They can be processed by the camera probe 20 itself and/or the controller 22 and/or host PC 23 and/or another processor device. In the embodiment described, the CMM 10 obtains the position and orientation of the camera probe 20 at the point images are obtained. This position and orientation information can be used during said processing in order to determine metrology information about the feature of interest. This position and orientation information can be used to determine the location of the feature of interest in the CMM's 10 measurement volume.

In the embodiments described above, such tracking occurs for a period before and after the acquisition point (e.g. for a period before and after the exposure time for the image). However, as will be understood, the invention could comprise merely turning the camera probe so as to track the feature of interest whilst acquiring the image at the acquisition point, e.g. for the exposure time for the image.

The camera probe 20 could configured to only acquire a single image of the feature of interest, i.e. at the predetermined acquisition point. Optionally, the camera probe 20 could be configured to obtain a plurality of images as it moves along the inspection path. The camera probe 20 could be configured to obtain a continuous stream of images as it moves along the inspection path. For instance, the camera probe 20 could be configured to obtain a video stream as it moves along the inspection path.

Figure 5:
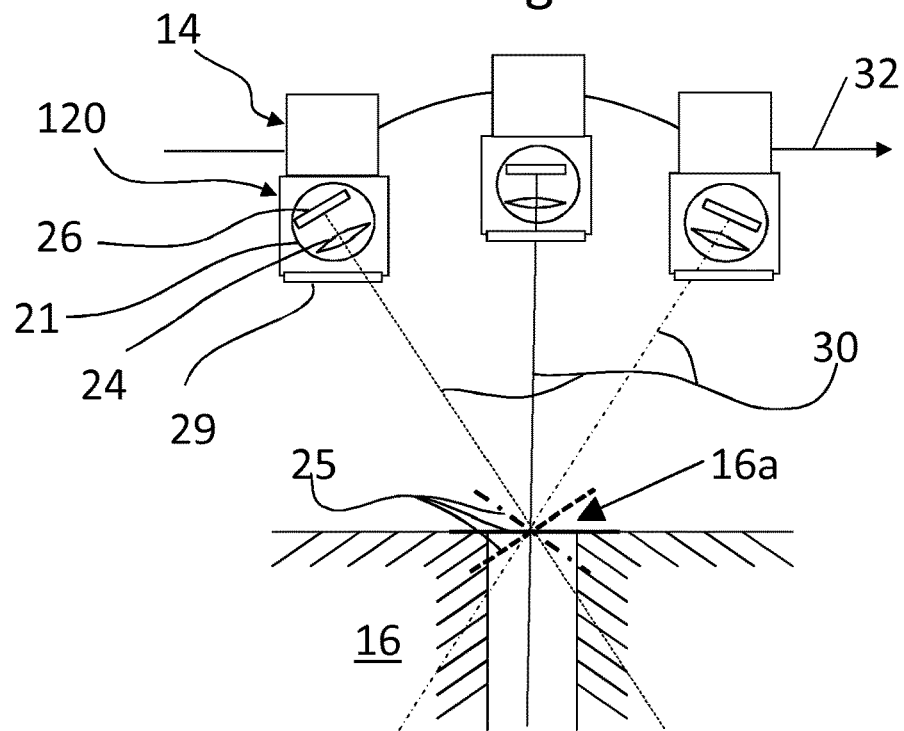
FIG. 5 illustrates turning a part within the camera probe so as to track a feature on an object being inspected according to the present invention.
Figure 6:
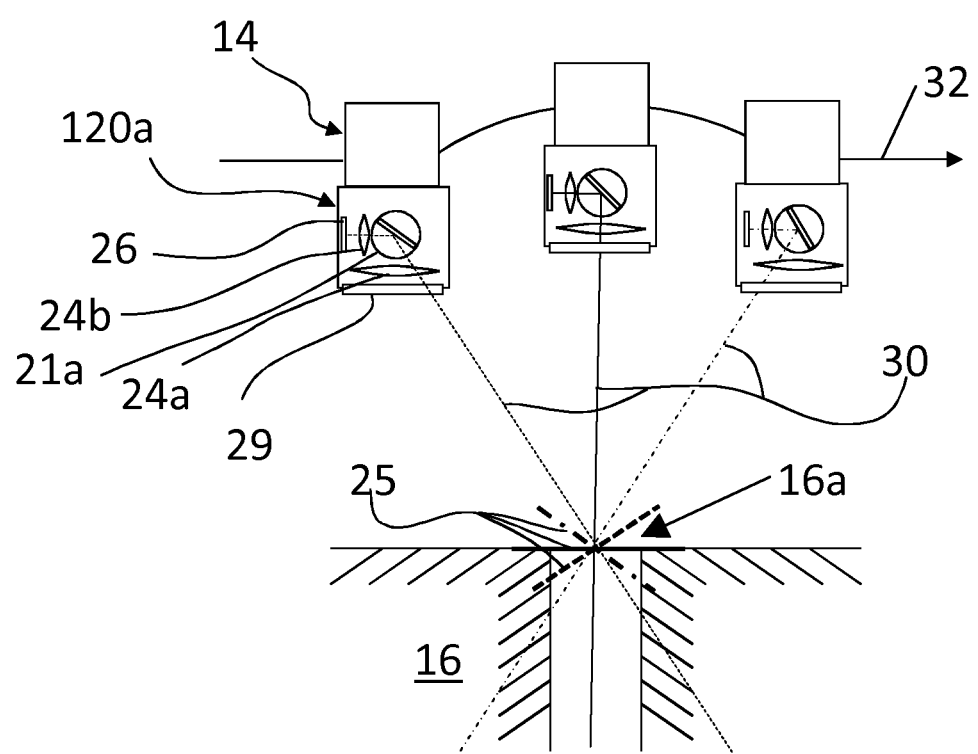
FIG. 6 illustrates another embodiment in which a part can be turned within the camera probe so as to track a feature on an object being inspected according to the present invention.

In the embodiments described above, the whole camera probe 20 is rotated in order to track the feature of interest. However, as will be understood, this need not necessarily be the case. For instance, in the embodiment of FIG. 5, the camera probe 120 is directly mounted to the quill 14 (e.g. rather than via an articulated head as in FIGS. 1 to 4). However, the camera probe 120 comprises a large window 29 and the optical system, in this case its lens 24 and sensor 26 are mounted in a rotatable unit 21. In accordance with the invention, as the quill 14 moves the camera probe 120 along the inspection path 32, the rotatable unit 21 causes the lens 24 and sensor 26 to track the feature of interest (e.g. the mouth of the bore 16a), in particular in this case such that the feature of interest stays centred on the sensor 26. As another example, in the embodiment of FIG. 6, in which the camera probe 120a comprises a pair of lenses 24a and 24b and a rotatable mirror 21 located between the pair of lenses 24a, 24b. Lens 24a (which could be lens assembly comprising a number of lenses) has appropriate magnification to produce an image of the object which is the correct size for the image sensor 26 and collimates the light from the object (e.g. produces an image focused at co ("infinity")). Rotating mirror 21b rotates to keep the image of the feature of interest on the object nominally static on the image sensor 26 as the camera probe 120a passes the feature of interest. Lens 26b takes the collimated light from the object and focuses it to a real image on the image sensor.

In the embodiments described above, the object is mounted on a stationary bed of the CMM. However, this does not need to be the case. For example the object could be mounted on a moving part of the CMM. For example, the object could be mounted on a rotatable part of the CMM, e.g. on a rotary table. In such an example the camera probe could be held in a fixed lateral position during operation (but still able to rotate about at least one axis). For example the camera probe could be mounted on an articulated head with at least one rotational axis and positioned and oriented so as to face and view an object mounted on the rotary table. The camera probe could be mounted on a laterally moveable part of the CMM (e.g. on the quill 14) but held laterally stationary during an inspection, or could even be mounted on an articulated head which in turn is mounted on a non-moveable part of the CMM. In any case, during an inspection routine, the object can be rotated by the rotary table and the camera probe (which is held in a fixed lateral position) can be continuously turned so as to track a feature on the object as the feature moves past the camera probe, thereby slowing the passage of the feature across the camera probe's sensor in the same way as described above in connection with the other embodiments. Also in the same way as described above in connection with the other embodiments of the invention, if the object has multiple features of interest, e.g. multiple bores, then the camera probe can be turned back and forth, such that after tracking one feature, it can be turned toward the next approaching feature so as to begin to track the next feature.

Accordingly, as will be understood, an inspection path can refer to the path that the object (in particular the feature(s) of interest) takes during an inspection routine. Furthermore, both the camera probe and object could be moved during an inspection routine, in which case the inspection path can refer to the path of both the camera probe and object (in particular the feature(s) of interest) during an inspection routine.

In the embodiments described above, the tracking of the feature of interest is such that the feature of interest is kept substantially in the centre of the camera's field of view. However, as will be understood, this need not necessarily be the case. For example, a point on the feature of interest can be kept substantially laterally stationary at an off-centre position within the camera's field of field. Furthermore, the feature of interest need not be kept substantially laterally stationary. Rather, the method of the invention could comprise merely turning the probe (or a part of the probe) so as to track the feature of interest so as to slow (rather than substantially stop) the passage of the feature of interest across the camera probe's field of view.

As described in the above embodiments, at least one image (e.g. one or more images) (of the feature of interest) is obtained whilst at least part of the camera probe is rotated (so as to slow the passage of the feature of interest across the camera probe's field of view). As will be understood, if desired, a plurality of images can be obtained whilst at least part of the camera probe is rotated (so as to slow the passage of the feature of interest across the camera probe's field of view).

The invention claimed is:

1. A method of measuring an object with a camera probe for capturing an image of an object, the camera probe and object being movable relative to each other by a measurement apparatus comprising a coordinate positioning machine, at least a part of the camera probe being rotatable about at least one axis, the method comprising:
   a) the measurement apparatus moving the camera probe and the object relative to each other; and
   b) for at least one period during said relative movement turning at least a part of the camera probe about the at least one axis thereby slowing the passage of a feature of interest to be measured on the object across the camera probe's field of view, and capturing at least one image of the feature of interest during at least a portion of said turning.

2. A method as claimed in claim 1, in which at least a part of the measurement apparatus is rotatable about at least one axis, the camera probe being rotated by the measurement apparatus about the at least one axis.

3. A method as claimed in claim 1, comprising capturing at least one image of the feature of interest at a predetermined relative position between the camera and feature of interest.

4. A method as claimed in claim 3, comprising turning at least a part of the camera probe about the at least one axis at least one of before and after the predetermined relative position.

5. A method as claimed in claim 1, comprising capturing a plurality images of the predetermined feature of interest whilst at least a part of the camera probe turns about the at least one axis.

6. A method as claimed in claim 1, in which during such turning the feature of interest is kept within the camera probe's field of view.

7. A method as claimed in any claim 6, in which during such turning the feature of interest is kept substantially laterally stationary within the camera probe's field of view.

8. A method as claimed in claim 1, in which the camera probe is moved relative to the feature of interest so as to keep the feature of interest within the camera probe's depth of field during such turning.

9. A method as claimed in claim 1, in which the camera probe's optical axis leads the camera probe as the camera probe and feature of interest at least one of approaches and trails the camera probe after the camera probe and the feature of interest have passed each other.

10. A method as claimed in claim 1, in which such turning comprises, controlling the camera probe such that the camera probe pivots about a point in the camera probe's depth of field.

11. A method as claimed in claim 1, comprising for each of a plurality of predetermined features of interest on the object, the measurement apparatus turning at least a part of the camera probe about the at least one axis, thereby slowing the passage of the predetermined feature of interest past the camera probe's field of view, and capturing at least one image of the predetermined feature of interest.

12. A method as claimed in claim 1, in which the predetermined feature of interest comprises a bore.

13. A method as claimed in claim 1, comprising using the at least one image, and position data obtained from the measurement apparatus regarding the position of the camera probe at the point the at least one image was obtained in order to obtain measurement data concerning the feature of interest.

14. A method of inspecting an object with a camera probe which move relative to each other during the capturing of an image of a feature of interest of the object, the method comprising turning at least a part of the camera probe so as to counter the relative motion and so that the camera probe tracks the feature of interest during the capturing of the image of the feature of interest.

15. A method of capturing at least one image of each of a plurality of features of interest on an object with a camera probe which move relative to each other during image capture, comprising for each of said plurality of features of interest on the object the measurement apparatus turning at least a part of the camera probe during image capture, thereby slowing the passage of the feature of interest being captured past the camera probe's field of view.

16. A computer program code comprising instructions which when executed by a controller of a measurement apparatus causes the measurement apparatus to operate in accordance with the method of claim 1.

17. A computer storage medium comprising computer program code which when executed by a controller of a measurement apparatus causes the measurement apparatus to operate in accordance with the method of claim 1.

18. An apparatus for measuring an object comprising a camera probe mounted on a measurement apparatus comprising a coordinate positioning machine, at least a part of the camera probe being rotatable about at least one axis, the apparatus comprising a controller which is configured to control the measurement apparatus so as to move the camera probe and object relative to each other, and, for at least one period during said relative movement turn said at least a part of the camera probe about the at least one axis thereby slowing the passage of a feature of interest to be measured across the camera probe's field of view, and configured to control the camera probe so as to capture at least one image of the feature of interest during at least a portion of such turning.

19. A method as claimed in claim 1, wherein capturing at least one image of the feature of interest during a portion of said turning comprises capturing at least one image of the feature of interest over a duration of time.

* * * * *